United States Patent
Gittard et al.

(10) Patent No.: US 9,681,970 B2
(45) Date of Patent: Jun. 20, 2017

(54) SYSTEMS AND METHODS FOR DEPOLYING AN ENDOLUMINAL SLEEVE FIELD

(71) Applicant: Cook Medical Technologies LLC, Bloomington, IN (US)

(72) Inventors: Shaun D. Gittard, Winston-Salem, NC (US); John Crowder Sigmon, Jr., Winston-Salem, NC (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 493 days.

(21) Appl. No.: 14/084,233

(22) Filed: Nov. 19, 2013

(65) Prior Publication Data

US 2014/0142719 A1     May 22, 2014

Related U.S. Application Data

(60) Provisional application No. 61/728,483, filed on Nov. 20, 2012.

(51) Int. Cl.
    *A61F 2/04*        (2013.01)
    *A61F 2/958*      (2013.01)
    *A61F 5/00*        (2006.01)

(52) U.S. Cl.
    CPC ............ *A61F 2/958* (2013.01); *A61F 2/04* (2013.01); *A61F 5/0076* (2013.01)

(58) Field of Classification Search
CPC ............ A61B 17/22; A61B 17/3207; A61B 17/22031; A61B 2017/22039; A61B 2217/005; A61B 2017/22094; A61B 2017/22041; A61B 2017/22038; A61B 2017/22079; A61M 5/31511; A61M 1/0035; A61F 2/958; A61F 5/0076; A61F 2/04; A61F 2002/045; A61F 2/042; A61F 2/043; A61F 2/044; A61F 2/045; A61F 2/046; A61F 2/047; A61F 2/048; A61F 2/06; A61F 2/064; A61F 2/07; A61F 2002/041; A61F 2002/072; A61F 2002/075; A61F 2002/077; A61F 2002/9583

See application file for complete search history.

(56) References Cited

U.S. PATENT DOCUMENTS

| | | | |
|---|---|---|---|
| 5,211,654 A | * | 5/1993 | Kaltenbach ......... A61M 25/104 604/913 |
| 5,667,479 A | | 9/1997 | Kieturakis |
| 6,544,278 B1 | | 4/2003 | Vrba et al. |

(Continued)

OTHER PUBLICATIONS

European Search Report for related European Application No. 13193725.2, mailed Jan. 24, 2014 (7 pages).

*Primary Examiner* — Todd J Scherbel
(74) *Attorney, Agent, or Firm* — Brinks Gilson & Lione

(57) ABSTRACT

A device and method for deploying an endoluminal sleeve is disclosed. The endoluminal sleeve has a proximal end that is rolled with a thread. The distal end is disposed about a balloon and can be expanded to contact the lumen wall. An adhesive holds the sleeve in place and the endoluminal sleeve is unrolled. The balloon is deflated and moved to a second location. The balloon is then inflated again expanding the endoluminal sleeve proximate the second location.

12 Claims, 10 Drawing Sheets

(56) References Cited

U.S. PATENT DOCUMENTS

| | | | |
|---|---|---|---|
| 2002/0165603 A1* | 11/2002 | Thornton | A61F 2/06 623/1.13 |
| 2007/0250087 A1 | 10/2007 | Makower et al. | |
| 2007/0289596 A1* | 12/2007 | Campbell | A61M 16/04 128/207.15 |
| 2008/0195226 A1 | 8/2008 | Williams et al. | |
| 2008/0255678 A1 | 10/2008 | Cully et al. | |
| 2008/0287907 A1 | 11/2008 | Gregory et al. | |
| 2009/0012553 A1 | 1/2009 | Swain et al. | |
| 2011/0009801 A1 | 1/2011 | Blaeser et al. | |
| 2011/0034987 A1* | 2/2011 | Kennedy | A61F 2/95 623/1.11 |
| 2011/0137428 A1 | 6/2011 | Terliuc | |
| 2012/0116286 A1 | 5/2012 | Williams et al. | |
| 2012/0123529 A1* | 5/2012 | Levi | A61F 2/2412 623/2.11 |
| 2013/0197622 A1* | 8/2013 | Mitra | A61F 2/07 623/1.15 |

* cited by examiner

SYSTEMS AND METHODS FOR DEPOLYING AN ENDOLUMINAL SLEEVE FIELD

PRIORITY CLAIM

This application claims the benefit of and priority from U.S. Provisional Patent Application No. 61/728,483 filed on Nov. 20, 2012, which is hereby incorporated in its entirety for all purposes by this reference.

FIELD OF INVENTION

Embodiments of the present invention relate to the field of implants for treating obesity and Type II diabetes. More specifically embodiments of the present invention relate to systems and methods for deploying implants for reducing the ability of the body to absorb nutrients.

BACKGROUND

The human body absorbs nutrients through the digestive system. Food is introduced through the mouth where a person's teeth masticate the food into smaller pieces. Saliva in the mouth begins the digestion of starch in the food. A person then swallows the food, transporting the food through the esophagus into the stomach. In the stomach, the food is mixed with gastric juice which begins the digestion of protein in the food. The stomach mixes the food with other enzymes. After a period of time, the pyloric sphincter opens at the bottom of the stomach allowing the food to pass into the duodenum where the food mixes with more enzymes. The food continues into the small intestine, where digestion continues and nutrients are adsorbed into the bloodstream. The large majority of the absorption of nutrients occurs in the small intestine. The remaining material is transported to the large intestine where water is absorbed before waste is eliminated from the body.

Reducing the ability of the body to absorb nutrients has been shown to be an effective means of weight loss and treatment of Type II diabetes. Past treatments for reducing the ability of the body to adsorb nutrients included gastric bypasses, in which the functional volume of the stomach is reduced, and intestinal and/or stomach sleeves, in which the sleeves inhibit the absorption of nutrients. Current intestinal sleeves are placed proximate the pyloric sphincter, with part of the intestinal sleeve in the distal end of the stomach and part of the intestinal sleeve in the duodenum. Current devices may cause sores in the stomach and intestine from the intestinal sleeve rubbing and cutting into tissue as well as twisting and subsequent stricture of the sleeve.

SUMMARY

Embodiments of the invention include a method for delivering an endoluminal sleeve. The method includes introducing a catheter assembly into a body lumen where the catheter assembly comprising a balloon catheter having a distal portion with a balloon and a proximal portion, a sleeve disposed about the distal portion of the balloon catheter, the sleeve having a rolled portion with a thread disposed therein and an unrolled portion disposed about the balloon, the thread extending from the rolled portion to the distal portion of the balloon catheter. The catheter is then positioned proximate a first location within the body lumen. The balloon is inflated expanding the unrolled portion of the sleeve to contact a wall of the body lumen at the first location. A first expanded portion of the sleeve is adhered to the wall of the body lumen at the first location. The thread is tensioned while the first expanded portion of the sleeve is adhered to the wall of the body lumen at the first location causing the sleeve to unroll at least partially. The tension is then relaxed in the thread. The balloon is deflated subsequent to adhering the first expanded portion of the sleeve to the wall of the body lumen at the first location. The catheter is moved to a second location within the body lumen. The balloon is inflated expanding a second portion of the sleeve to contact the wall of the body lumen at the second location. The second portion of the sleeve is adhered to the wall of the body lumen at the second location.

Embodiments further include a method for preparing a catheter assembly for delivery of an endoluminal sleeve. An endoluminal sleeve having a tubular shape with an interior surface, an exterior surface opposite the interior surface, an axis, a proximal end, and a distal end is provided. The endoluminal sleeve is positioned about a mandrel, wherein the exterior surface faces the mandrel defining a lumen and the interior surface faces away from the mandrel. A thread is laid along the interior surface in an axial direction from the proximal end to a location past the distal end of the endoluminal sleeve. The proximal end of the endoluminal sleeve is rolled about the mandrel towards the distal end of the endoluminal sleeve resulting in a partially rolled endoluminal sleeve having a rolled portion disposed and an unrolled portion. The partially rolled endoluminal sleeve is inverted positioning the interior surface of unrolled portion inside the partially rolled endoluminal sleeve to define a lumen and positioning the rolled portion and the thread inside the lumen. The partially rolled endoluminal sleeve is positioned about a balloon catheter with the unrolled portion positioned over a balloon of the balloon catheter wherein the interior surface of the unrolled portion faces the balloon catheter.

Embodiments further include a catheter assembly for deploying an endoluminal sleeve. The catheter assembly includes a balloon catheter having a distal portion and a proximal portion, a balloon disposed at the distal portion of the balloon catheter, and an endoluminal sleeve disposed about the distal portion of the balloon catheter. The endoluminal sleeve has a rolled portion rolled inward towards an axis of the balloon catheter with a thread disposed in the rolled portion and an unrolled portion disposed about the balloon, the thread extending from within the rolled portion to the distal portion of the balloon catheter.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which.

The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. The embodiments will be described in relation to an intestinal sleeve, but one of ordinary skill in the art would recognize that the system and methods are applicable more generally to an endoluminal sleeve and the deployment of the endoluminal sleeve in a body lumen. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Additional advantages of the present invention will become readily apparent from the following discussion, particularly when taken together with the accompanying drawings.

Figure 1:
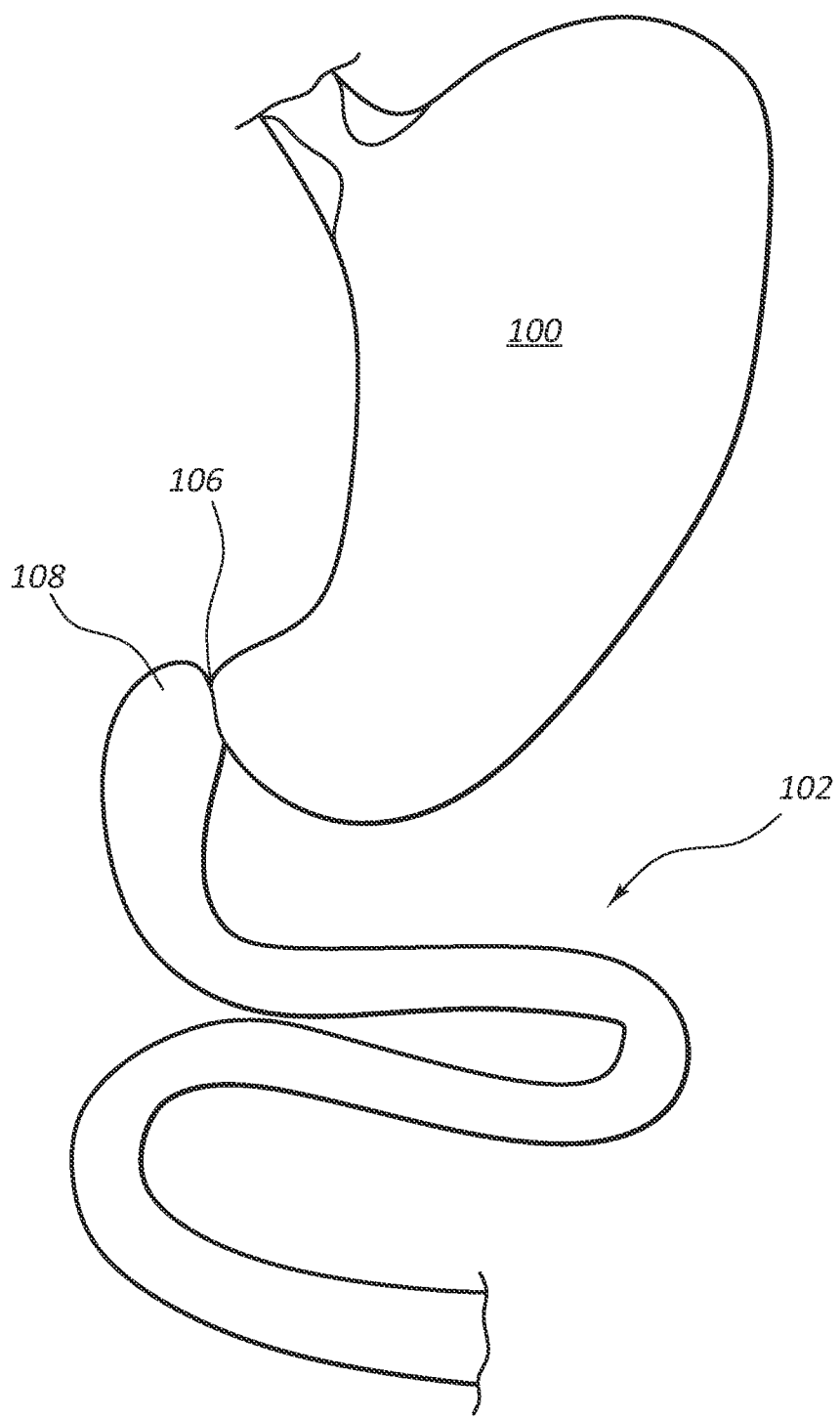
FIG. 1 is a schematic of a stomach and upper lower intestine including the duodenum.

FIG. 1 is a cross-sectional schematic of a stomach 100 and a portion of a small intestine 102. A ring like muscle, the pyloric sphincter 106, separates the interior of the stomach 100 and the interior of the small intestine 102. In a contracted state, the pyloric sphincter 106 inhibits material from passing between the stomach 100 and the small intestine 102. When the pyloric sphincter 106 relaxes, the content of the stomach 100 may be passed into the small intestine 102. Just beyond the pyloric sphincter 106 is the first section of the small intestine 102, termed the duodenum 108.

Figure 2:
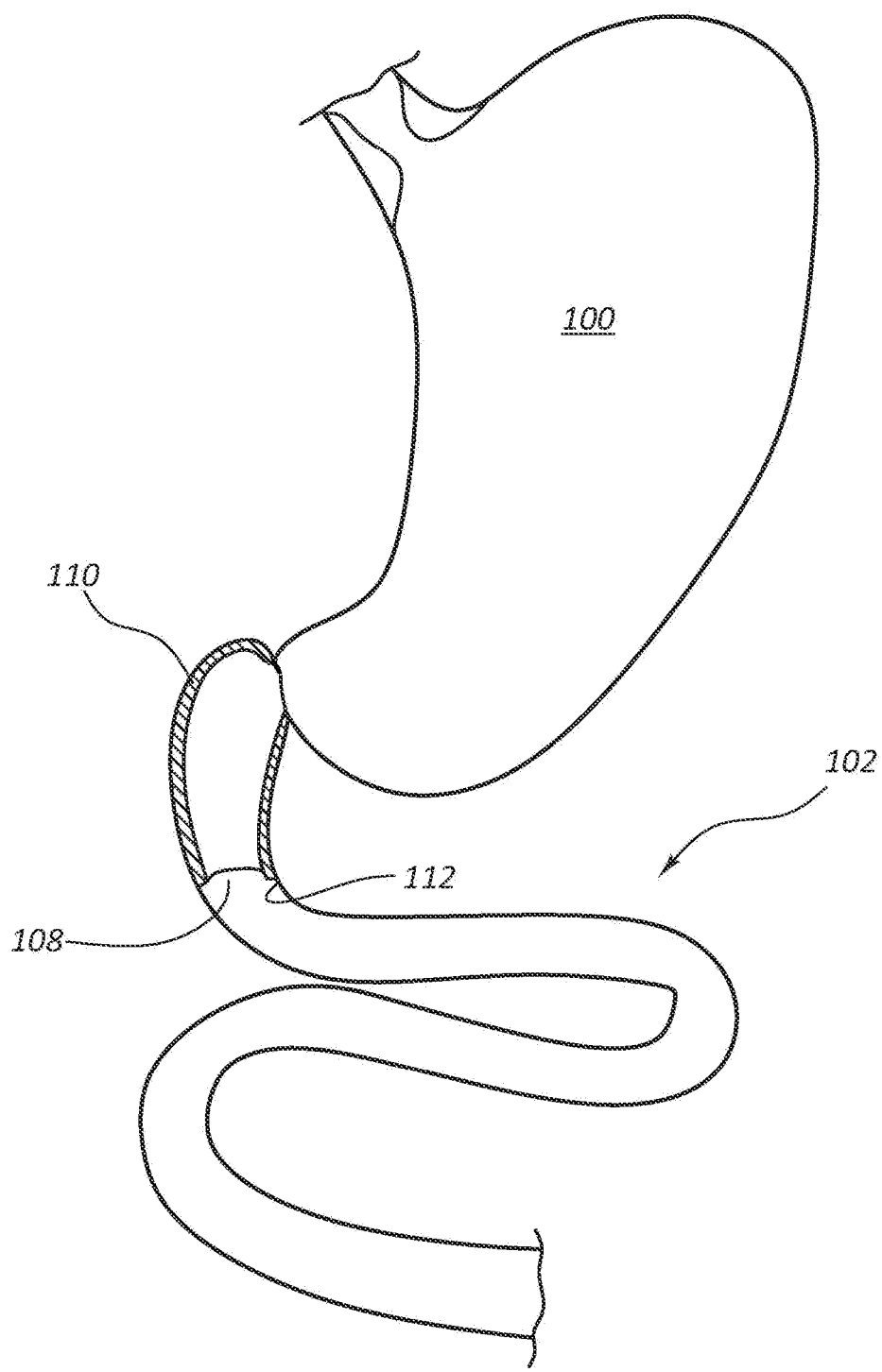
FIG. 2 is a schematic of a stomach and upper lower intestine including the duodenum illustrating an intestinal sleeve deployed in the duodenum.

FIG. 2 is a cross-section schematic of the stomach 100 of FIG. 1, showing an embodiment of an intestinal sleeve 110 fixed in place. The intestinal sleeve 110 is comprised of a thin, impermeable elastic or plastic membrane adhered to a wall 112 of the duodenum 108. Nutrients passing from the stomach 100 into the duodenum 108 are inhibited from absorption by the intestinal sleeve 110.

Figure 3:
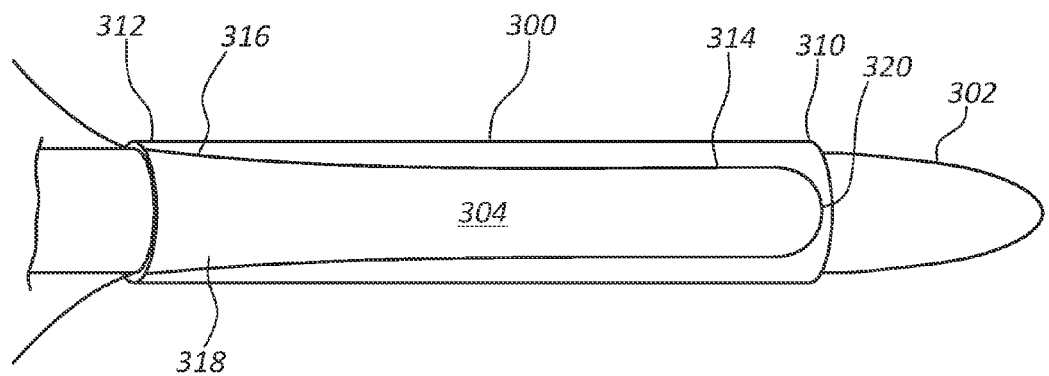
FIG. 3 is a schematic of an intestinal sleeve disposed about a mandrel.
Figure 3A:
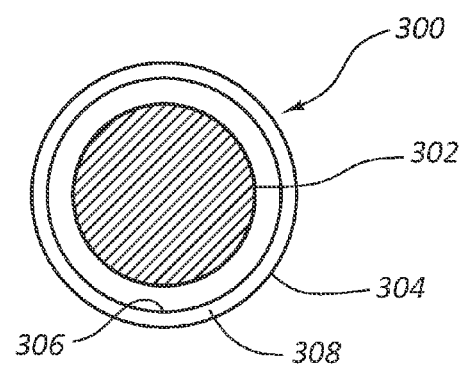
FIG. 3a is a cross sectional schematic of the intestinal sleeve of FIG. 3.

FIG. 3 illustrates an intestinal sleeve 300 and a mandrel 302. FIG. 3a illustrates a cross section of the intestinal sleeve 300 disposed about the mandrel 302. The intestinal sleeve 300 has an interior surface 304 and an exterior surface 306 separated by a membrane 308. The intestinal sleeve 300 is initially inside out, such that the interior surface 304 is on the outside of the intestinal sleeve 300. In this inside out configuration, the exterior surface 306 defines an inner diameter of the intestinal sleeve 300. The intestinal sleeve 300 further has a proximal end 310 and a distal end 312. The mandrel 302 is sized to be inserted into the inner diameter of the intestinal sleeve 300.

In preparing the intestinal sleeve 300 for use, the intestinal sleeve 300 is positioned over the mandrel 302 as shown in FIG. 3. A thread 314 is laid along the internal surface 304 of the intestinal sleeve 300. The thread may be a suture, a thin wire, a strip of material, a string, or any elongated flexible member. The thread 314 has a first end section 316, a middle section 318, and a second end section 320. The thread 314 is laid out such that the first end section 316 and the second end section 320 are on opposite sides of the mandrel 302. The middle section 318 is disposed near the proximal end 310 of the intestinal sleeve 300. The first end section 316 and the second end section 318 extend longitudinally along the interior surface 304 and past the distal end 312 of the intestinal sleeve 300.

The mandrel 302, intestinal sleeve 300, and thread 314 may then be placed in a basin of mucoadhesive powder to distribute the mucoadhesive powder about the intestinal sleeve 300. Other techniques of applying the mucoadhesive powder are possible and embodiments of the invention are not limited to the use of a basin of mucoadhesive powder.

Figure 4:
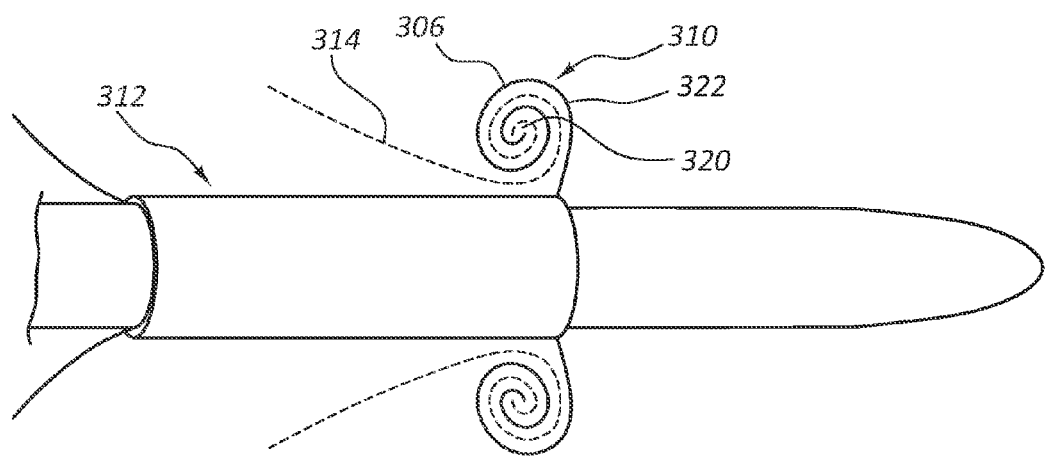
FIG. 4 is a schematic of the intestinal sleeve of FIG. 3 with the proximal end being partially rolled.

FIG. 4 illustrates the intestinal sleeve 300 of FIG. 3 being rolled about the mandrel 302. The intestinal sleeve 300 may be rolled about the mandrel 302 while submersed in the basin of mucoadhesive powder. The intestinal sleeve 300 is rolled about the mandrel 302 from the proximal end 310 toward the distal end 312. The mucoadhesive powder is trapped within the rolls 322 and the inner surface 306 of the intestinal sleeve 300 is exposed on the outside of the roll 322. The thread 314 (shown as a dashed line for clarity) is trapped within the roll 322 as well, with the middle portion 320 of the thread 314 being located in the innermost part of the roll 322 near the proximal end of the intestinal sleeve. The intestinal sleeve 300 is rolled short of the complete length of the intestinal sleeve 300 and may stop at a location near a mid-point of the intestinal sleeve 300. In other embodiments, the intestinal sleeve 300 may be rolled a distance greater or less than the mid-point of the intestinal sleeve 300. The distance the intestinal sleeve 300 is rolled may be dependent upon the relative size of the inner diameter compared to the length of the intestinal sleeve 300.

Figure 4A:
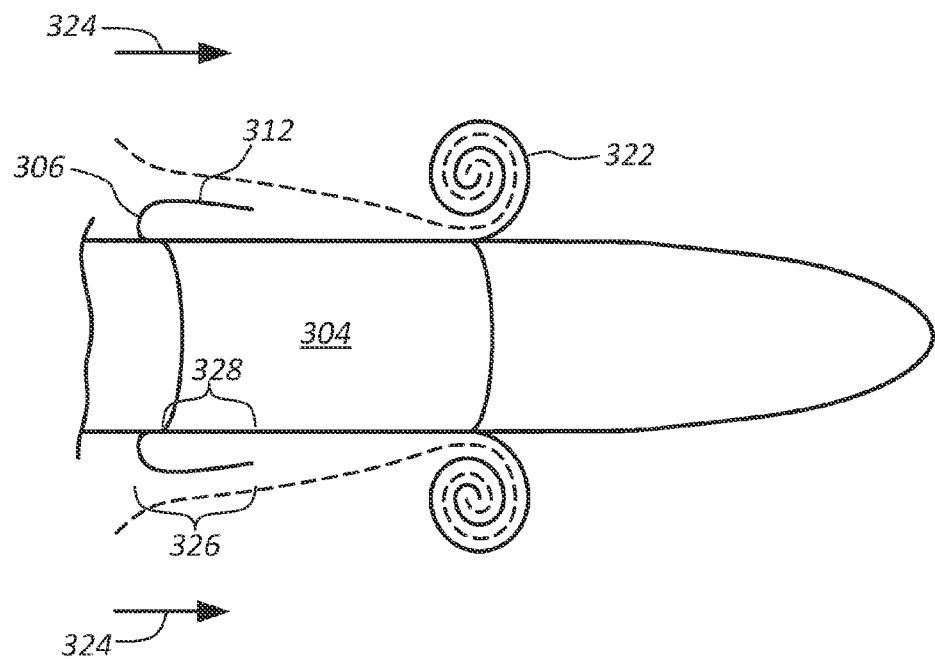
FIG. 4a is a schematic of the intestinal sleeve of FIG. 3 with the distal end being folded.
Figure 4B:
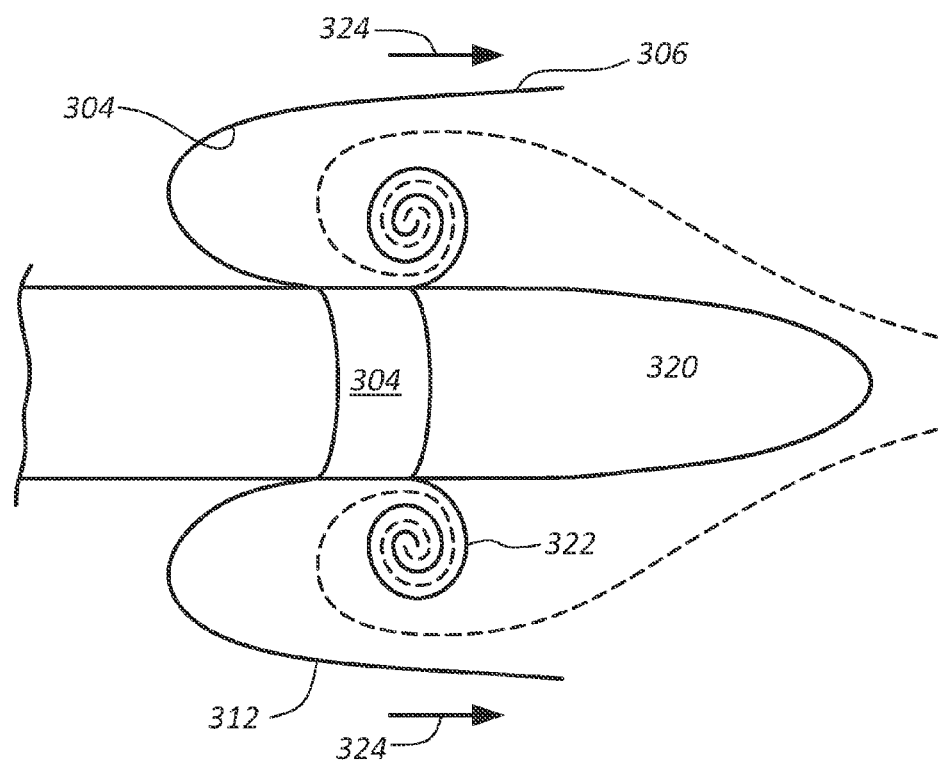
FIG. 4b is a schematic of the intestinal sleeve of FIG. 3 with the distal end being partially pulled over the proximal end.
Figure 4C:
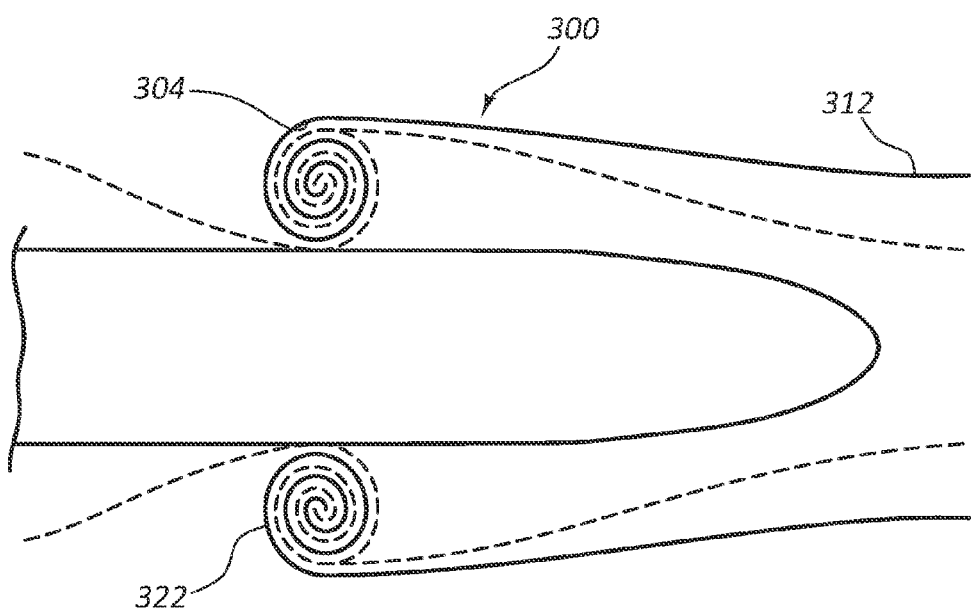
FIG. 4c is a schematic of the intestinal sleeve of FIG. 3 with the proximal end being pulled past the proximal end.

The partially rolled intestinal sleeve 300 is then inverted so that the outer surface 306 of the intestinal sleeve 300 is on the outside of the intestinal sleeve 300 and the inner surface 304 is on the inside of the intestinal sleeve 300. The roll 322 is then on the inside of the intestinal sleeve 300 with the thread 314 disposed on the inside as well. FIG. 4a through FIG. 4c illustrates a procedure for inverting the partially rolled intestinal sleeve 300.

In FIG. 4a, the distal end 312 of the partially rolled intestinal sleeve 300 is pulled over the inner surface 304 and toward the roll 322 formed on the mandrel 302 as shown by arrows 324. As the distal end 312 is pulled over the inner surface 304, the outer surface 306 is presented to the outside of the intestinal sleeve 300. A first portion 326 of the inner surface 304 of the intestinal sleeve 300 faces a second portion 328 of the inner surface 304 of the intestinal sleeve 300 and the first portion 326 of the outer surface 306 of the intestinal sleeve faces the outside. FIG. 4b illustrates the distal end 312 of the partially rolled intestinal sleeve 300 being pulled over the roll 322 that was formed on the mandrel 302.

FIG. 4c illustrates the distal end 312 of the intestinal sleeve 300 having been pulled past the roll 322. The distal end 312 of the intestinal sleeve 300 may be pulled until the inner surface 304 of the intestinal sleeve 300 contacts the roll 322. The intestinal sleeve 300 is now inverted from its previous configuration with the outer surface 306 now facing the outside of the intestinal sleeve 300 and the inner surface 304 facing the inside of the intestinal sleeve. The thread 314 is now on the inside of the intestinal sleeve 300 and may be pulled out of the proximal end 312 of the intestinal sleeve 300 past the roll 322. Thus, the thread 314 extends from the center of the roll 322 at which the proximal end 312 is located, is rolled around the roll 322, and exits the intestinal sleeve 300.

The distal end 312 of the partially rolled intestinal sleeve 300 may pulled over the roll 322 to invert the intestinal sleeve 300 while the intestinal sleeve 300 is on the mandrel 302, as shown in FIG. 4a through 4c, or in other embodiments, the intestinal sleeve 300 may be removed from the mandrel 302 prior to pulling the intestinal sleeve 300 over the roll 322.

Figure 5A:
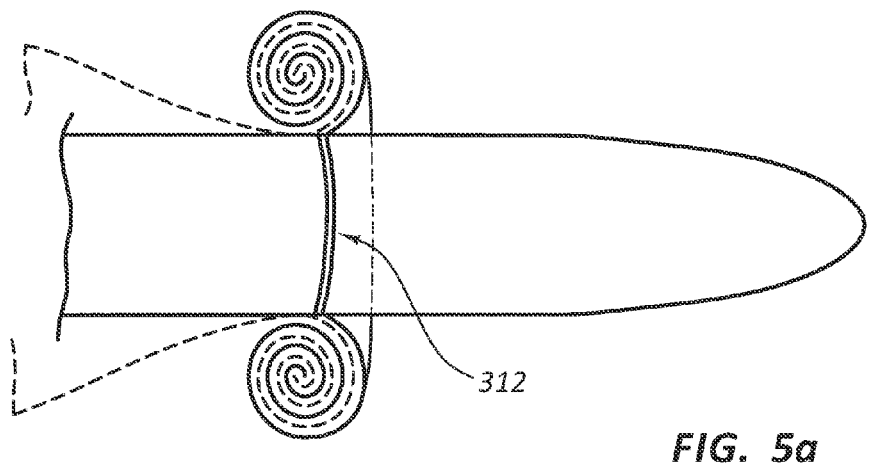
FIG. 5a is a schematic of the intestinal sleeve of FIG. 3 with the proximal end being rolled past the distal end.
Figure 5B:
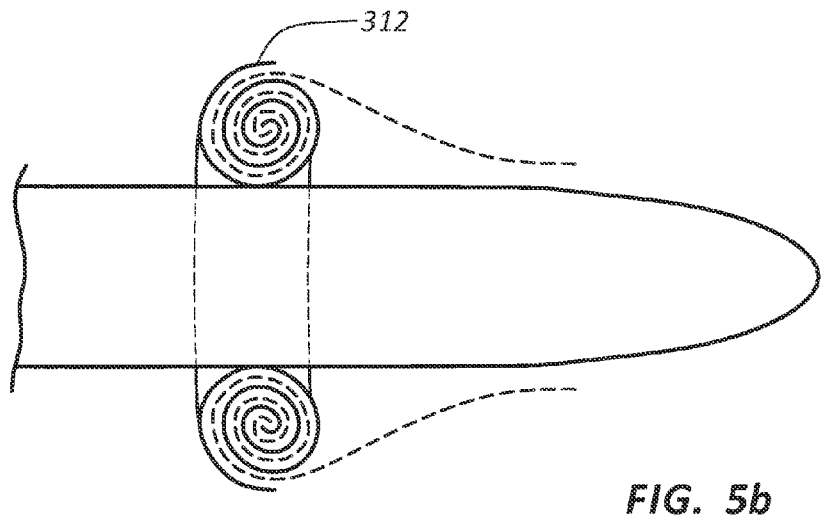
FIG. 5b is a schematic of the intestinal sleeve of FIG. 3 with the distal end being positioned on the outside of the roll.
Figure 5C:
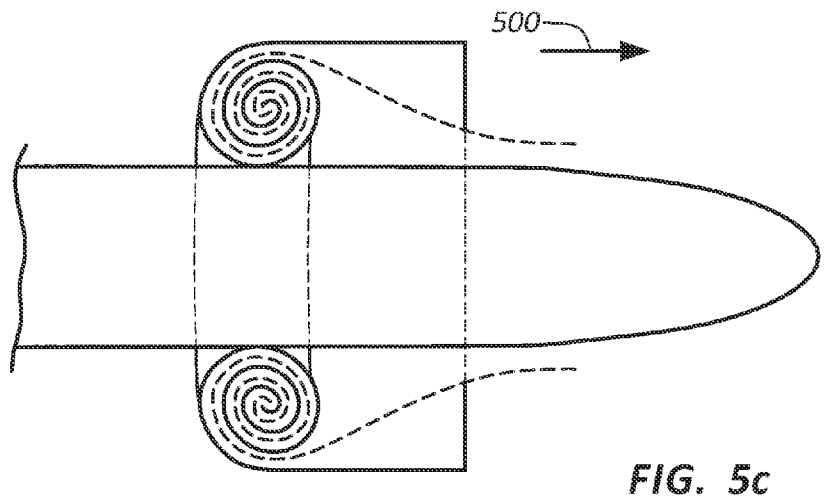
FIG. 5c is a schematic of the intestinal sleeve of FIG. 3 with the distal end being pulled from the roll.

FIGS. 5a through 5c illustrate another method for inverting the intestinal sleeve 300 of FIG. 4. In this embodiment the roll 322 is rolled past the distal end 312 of the intestinal sleeve 300 as shown in FIG. 5a. The distal end 312 of the intestinal sleeve 300 is now on the exterior of the roll 322, and the proximal end 310 of the intestinal sleeve 300 is at the innermost part of the roll 322. As shown in FIG. 5c, the distal portion end 312 of the intestinal sleeve 300 is then pulled in a longitudinal direction 500, partially unrolling the intestinal sleeve 300. The intestinal sleeve 300 is now inverted with the exterior surface 306 of the intestinal sleeve 300 on the outside of the intestinal sleeve 300 and the interior surface on the inside of the intestinal sleeve 300.

Figure 6:
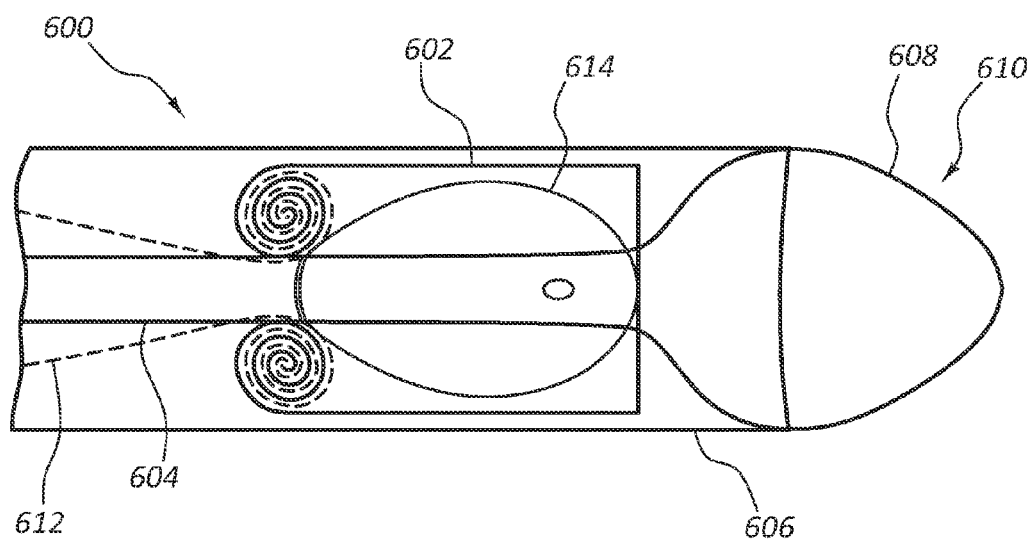
FIG. 6 illustrates an embodiment of a delivery system with an intestinal sleeve prepared for delivery.

FIG. 6 illustrates an embodiment of a delivery system 600 with an intestinal sleeve 602 prepared for delivery. The delivery system 600 is comprised of a balloon catheter 604 having a balloon 614, and the intestinal sleeve 602. The balloon catheter 604 may be housed within a sheath 606 and a dilator tip 608 may be disposed at a distal end 610 of the balloon catheter. Threads 612 extend from a proximal end 620 of the intestinal sleeve 602 and may extend the entire length of the balloon catheter 604. In other embodiments, the thread 612 may extend less than the entire length of the balloon catheter 604 and may be affixed to a separate actuator. For example, the thread 612 may be affixed to a sleeve (not shown) disposed proximal to the balloon 604. Refraction of the sleeve would tension the thread 612.

The delivery system 600 is guided to a deployment site such as the duodenum of the small intestine in the configuration of FIG. 6. The delivery system 600 may enter a body through a patient's oral cavity, be guided down the patient's esophagus, and pass through the stomach to the small intestine.

Figure 7:
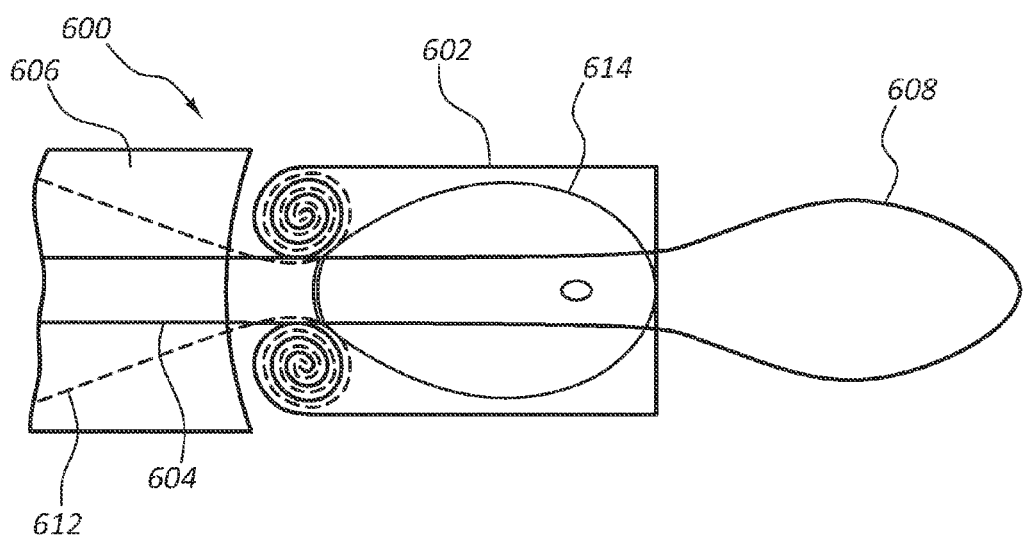
FIG. 7 illustrates the embodiment of FIG. 6 with a sleeve refracted for deployment of the intestinal sleeve.
Figure 8:
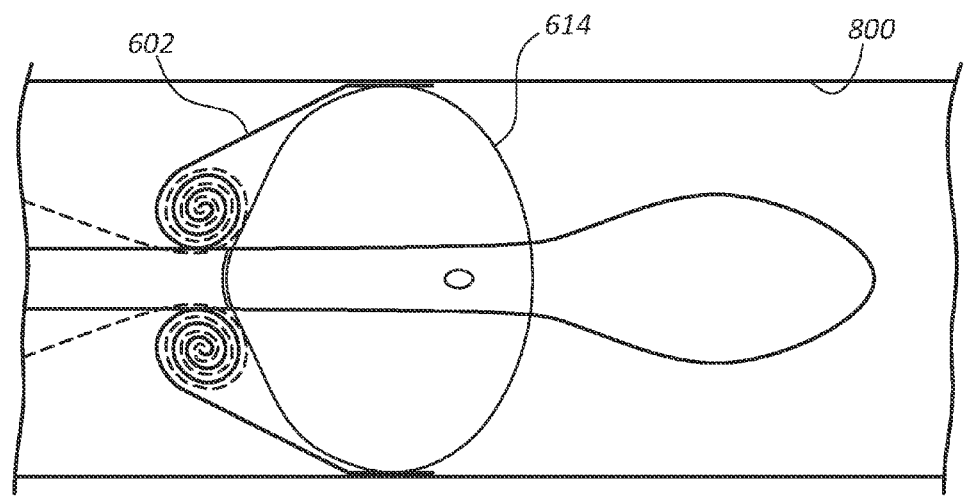
FIG. 8 illustrates the embodiment of FIG. 6 with a balloon expanding the intestinal sleeve.

When the delivery system 600 is positioned at the deployment site, the sheath 606 is retracted proximally exposing the intestinal sleeve 602 as shown in FIG. 7. The balloon 614 is then inflated as shown in FIG. 8, causing the intestinal sleeve 602 to expand radially until the intestinal sleeve 602 contacts a surface such as the intestinal wall 800. The balloon 614 presses a portion of the intestinal sleeve 602 against the intestinal wall 800. Mucoadhesive powder applied to the intestinal sleeve 602 adheres the portion of the intestinal sleeve 602 to the intestinal wall 800 resulting in an adhered portion 802.

Figure 9:
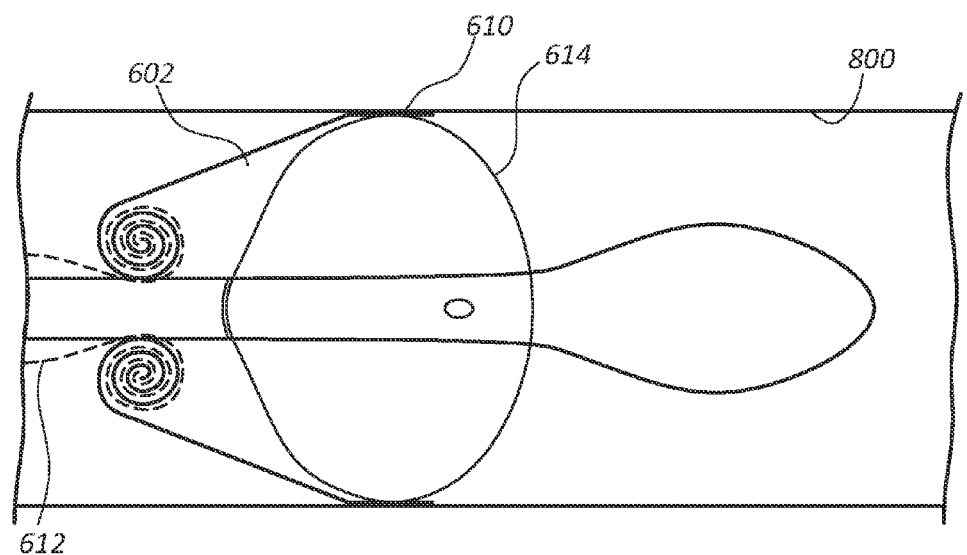
FIG. 9 illustrates the embodiment of FIG. 6 with a thread being tensioned to unroll the intestinal sleeve.
Figure 10:
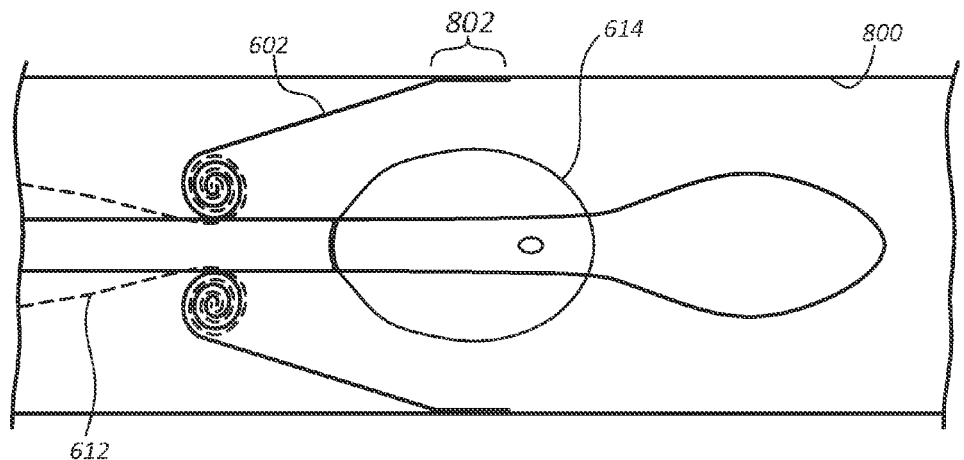
FIG. 10 illustrates the embodiment of FIG. 6 with the balloon deflated.
Figure 11:
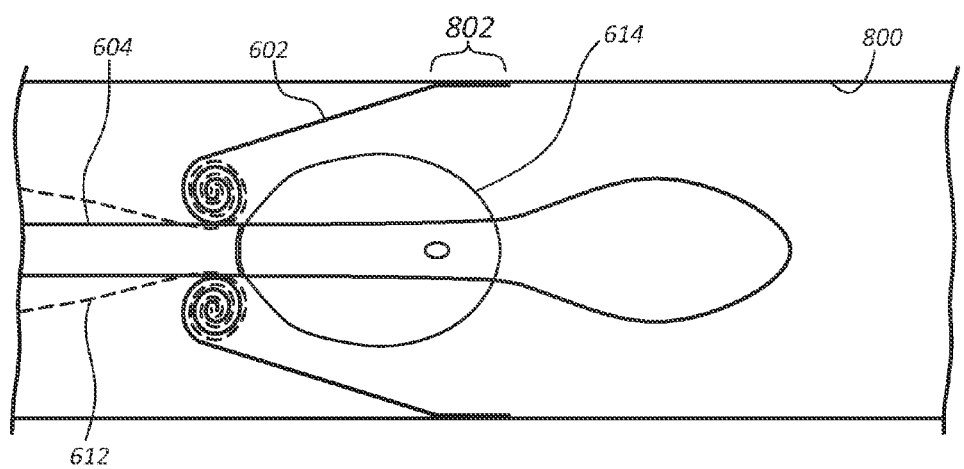
FIG. 11 illustrates the embodiment of FIG. 6 with the balloon catheter being repositioned.

In FIG. 9, the threads 612 are tensioned, partially unrolling the intestinal sleeve 602 in the proximal direction. When the intestinal sleeve 602 has been unrolled a desired distance, the tension is relaxed such that the intestinal sleeve 602 stops unrolling. The adhered portion 802 of the intestinal sleeve 602 remains in place due to the mucoadhesive adhesion and the pressure of the balloon 614. The balloon 614 is then deflated as shown in FIG. 10. The adhered portion 802 remains adhered to the intestinal wall 800. The balloon catheter 604 is then moved in the proximal direction, positioning the balloon 614 proximal to the adhered portion 802 as shown in FIG. 11.

Figure 12:
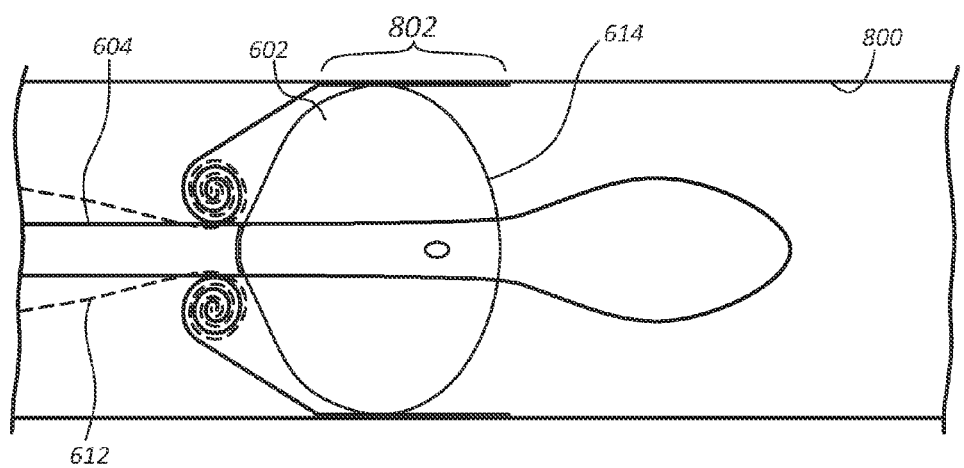
FIG. 12 illustrates the embodiment of FIG. 6 with the balloon being reflated to expand the intestinal sleeve.
Figure 13:
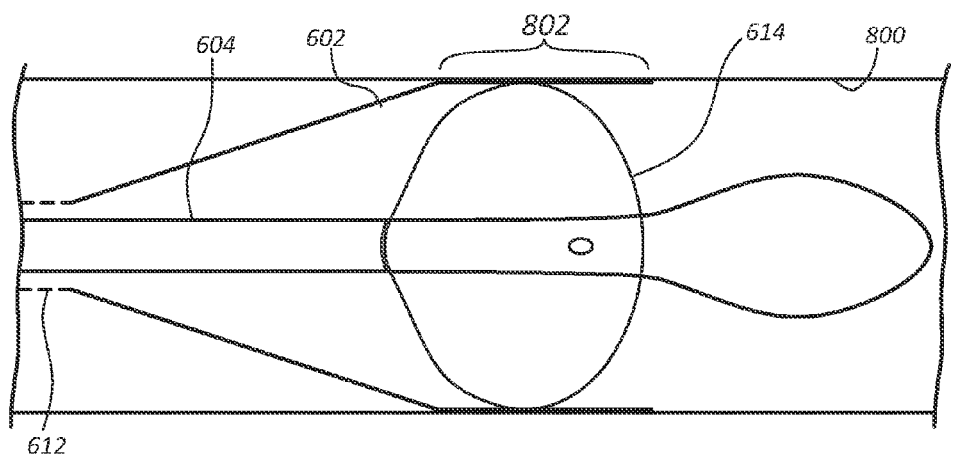
FIG. 13 illustrates the embodiment of FIG. 6 with tension applied to the threads to unroll the intestinal sleeve.

In FIG. 12 the balloon 614 is inflated proximal to the adhered portion 802, pressing the intestinal sleeve 602 into the intestinal wall 800. Another portion of the intestinal sleeve 602 adheres to the intestinal wall 800 resulting in the adhered portion 802 being enlarged. The threads 612 are again tensioned, further unrolling the intestinal sleeve 602. In some embodiments, the intestinal sleeve 602 may be unrolled completely, or in other embodiments, the tension may be relaxed once the intestinal sleeve 602 has unrolled a desired amount. In FIG. 13, the intestinal sleeve 602 has been unrolled completely, such that no roll is present.

In FIG. 13, the threads 612 are illustrated as being attached to the intestinal sleeve 602 after being completely unrolled, but in some embodiments the threads 612 may detach from the intestinal sleeve 602 once it is completely unrolled. In other embodiments, the mucoadhesive or other adhesive may lightly adhere the thread 612 to the intestinal sleeve 602. In such embodiments, further tension of the thread 612 will remove the thread 612 from the intestinal sleeve 602.

Figure 14:
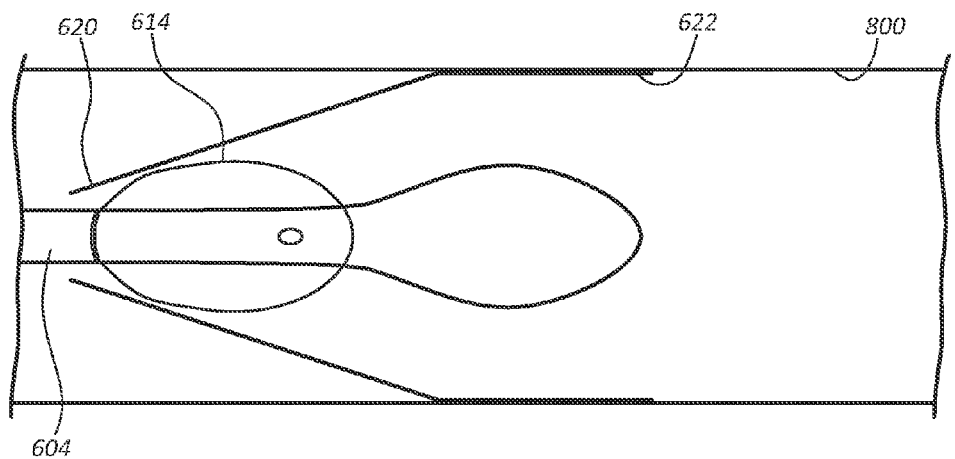
FIG. 14 illustrates the embodiment of FIG. 6 with the balloon being deflated and the balloon catheter repositioned.
Figure 15:
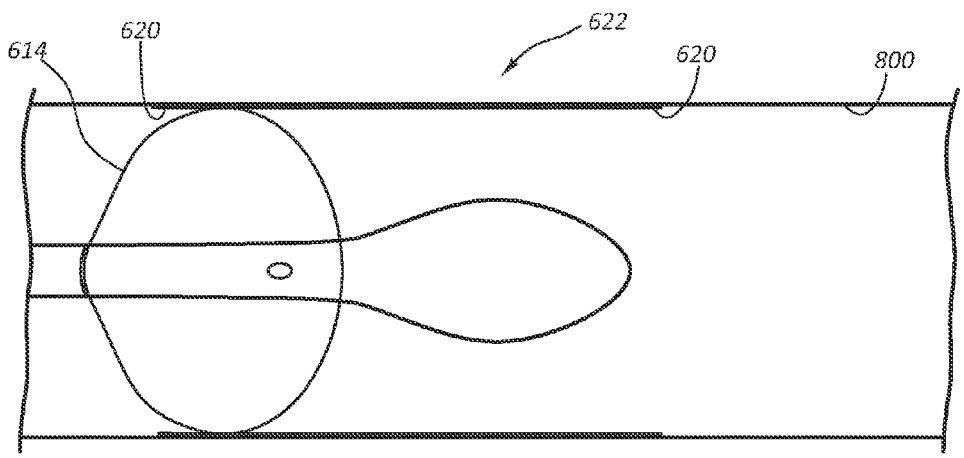
FIG. 15 illustrates the embodiment of FIG. 6 with the balloon being reflated to expand the intestinal sleeve.

FIG. 14 illustrates the thread 612 having been removed from the intestinal sleeve 602. The balloon 614 has been deflated and the balloon catheter 604 has been moved proximally, such that the balloon 614 is proximal to the adhered portion 802. The adhered portion 802 remains adhered to the intestinal wall 800. In FIG. 15 the balloon 614 is shown inflated, pressing the proximal end 620 of the intestinal sleeve 602 into the intestinal wall 800. The adhered portion 802 extends from a distal end 622 of the intestinal sleeve 602 to the proximal end 620 of the intestinal sleeve 602. The balloon 614 can then be deflated once again and the balloon catheter 604 may be removed from the lower intestine. The intestinal sleeve 602 remains in place due to the mucoadhesive adhering to the intestinal wall 800.

Embodiments of the invention have been described in relation to an intestinal sleeve, but are applicable to other endoluminal sleeves. Furthermore, other medical devices may be used in conjunction with the endoluminal sleeve. For example, deploying the endoluminal sleeve may be a part of a larger operation. It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A catheter assembly for deploying an endoluminal sleeve, the catheter assembly comprising:
   a balloon catheter having a distal portion and a proximal portion;
   a balloon disposed at the distal portion of the balloon catheter, the balloon expandable from a deflated configuration to an expanded configuration;
   an endoluminal sleeve disposed about the distal portion of the balloon catheter, the endoluminal sleeve being rolled longitudinally and having a rolled portion and an unrolled portion disposed about the balloon, the expanded configuration of the balloon expanding the unrolled portion of the balloon while leaving the rolled portion unexpanded; and
   a thread rolled within the rolled portion of the endoluminal sleeve and extending from within the rolled portion.

2. The catheter assembly of claim 1 further comprising a sheath disposed about the endoluminal sleeve.

3. The catheter assembly of claim 1 further comprising a tensioning mechanism adapted to tension the thread.

4. The catheter assembly of claim 3 wherein the adhesive is a mucoadhesive powder.

5. The catheter assembly of claim 1 wherein the endoluminal sleeve includes an adhesive adhered to the endoluminal sleeve.

6. The catheter assembly of claim 1 wherein the balloon catheter has a distal tip extending beyond the distal portion of the balloon catheter, the distal tip having at least one port disposed therein, wherein the thread extends from the rolled portion into the at least one port, and from the at least one port to the proximal portion of the balloon catheter.

7. A method for delivering an endoluminal sleeve, the method comprising:
   introducing a catheter assembly into a body lumen, the catheter assembly comprising a balloon catheter having a distal portion with a balloon and a proximal portion, a sleeve disposed about the distal portion of the balloon catheter, the sleeve being rolled longitudinally and having a rolled portion and an unrolled portion disposed about the balloon, and a thread rolled within the rolled portion of the sleeve and extending from the rolled portion to the proximal portion of the balloon catheter;
   positioning the catheter assembly proximate a first location within the body lumen;
   inflating the balloon and expanding the unrolled portion of the sleeve to contact a wall of the body lumen at the first location while leaved the rolled portion unexpanded;
   adhering a first expanded portion of the sleeve to the wall of the body lumen at the first location;
   tensioning the thread to unroll a portion of the rolled portion of the sleeve;
   deflating the balloon subsequent to adhering the first expanded portion of the sleeve to the wall of the body lumen at the first location;
   moving the catheter to a second location within the body lumen proximate the first expanded portion of the sleeve;
   inflating the balloon and expanding a second portion of the sleeve to contact the wall of the body lumen at the second location; and
   adhering the second portion of the sleeve to the wall of the body lumen at the second location.

8. The method of claim 7 further comprising:
   tensioning the thread while the second expanded portion of the sleeve is adhered to the wall of the body lumen at the second location causing the sleeve to unroll at least partially;
   relaxing the tension in the thread;
   deflating the balloon subsequent adhering the second expanded portion of the sleeve to the wall of the body lumen at the second location;
   moving the catheter to a third location within the body lumen proximate to the second expanded portion of the sleeve; and
   inflating the balloon and expanding a third portion of the sleeve to contact the wall of the body lumen at the third location; and
   adhering the third portion of the sleeve to the wall of the body lumen at the third location.

9. The method of claim 7 wherein deflating the balloon subsequent to adhering the first expanded portion of the sleeve to the wall of the body lumen at the first location is performed prior to tensioning the thread while the first expanded portion of the sleeve is adhered to the wall of the body lumen at the first location.

10. The method claim 7 wherein deflating the balloon subsequent to adhering the first expanded portion of the sleeve to the wall of the body lumen at the first location is performed subsequent to tensioning the thread while the first expanded portion of the sleeve is adhered to the wall of the body lumen at the first location.

11. The method of claim 7 further comprising removing the thread from the sleeve subsequent to adhering the second portion of the sleeve to the wall of the body lumen at the second location.

12. The method of claim 7 further comprising removing the balloon catheter from the body lumen subsequent to adhering the second portion of the sleeve to the wall of the body lumen at the second location.

* * * * *

UNITED STATES PATENT AND TRADEMARK OFFICE
CERTIFICATE OF CORRECTION

PATENT NO. : 9,681,970 B2  
APPLICATION NO. : 14/084233  
DATED : June 20, 2017  
INVENTOR(S) : Shaun D. Gittard et al.

Page 1 of 1

It is certified that error appears in the above-identified patent and that said Letters Patent is hereby corrected as shown below:

On the Title Page

In the Title, please delete "FIELD"

In the Claims

In Column 8, Claim 7, Line 5, delete "leaved" and replace with -- leaving --

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*